United States Patent [19]

Coyle et al.

[11] Patent Number: 5,594,340

[45] Date of Patent: Jan. 14, 1997

[54] APPARATUS FOR ACCURATELY CONTROLLING MOISTURE LEVELS OF AQUEOUS SURFACTANT COMPOSITIONS DURING ON LINE PROCESSING INCLUDING A CROSS-FEED PISTON ASSEMBLY

[75] Inventors: Laurie Coyle, North Arlington; Kevin M. Finucane, Saddle Brook, both of N.J.; James D. King, San Antonio, Tex.; Harold F. Donoho, San Antonio, Tex.; Armando De Los Santos, San Antonio, Tex.

[73] Assignee: Lever Brothers Company, Division of Conopco, Inc., New York, N.Y.

[21] Appl. No.: 302,285

[22] Filed: Sep. 8, 1994

[51] Int. Cl.[6] .................... G01V 3/18; G01N 1/14
[52] U.S. Cl. ........................... 324/321; 73/863.84
[58] Field of Search .................. 324/300, 306, 324/307, 309, 316, 321, 318; 128/653.2–653.5; 73/863.84, 863.83, 863.62, 863.71

[56] References Cited

U.S. PATENT DOCUMENTS

| | | | |
|---|---|---|---|
| 3,621,379 | 11/1971 | Watson et al. | 324/318 X |
| 3,966,973 | 6/1976 | Henry et al. | 324/307 |
| 4,527,436 | 7/1985 | Jones | 73/863.84 |
| 4,531,093 | 7/1985 | Rollwitz et al. | 324/306 |
| 4,663,070 | 5/1987 | Dobrovolny et al. | |
| 4,701,705 | 10/1987 | Rollwitz | 324/307 |
| 5,129,267 | 7/1992 | Nicholls | 324/321 X |
| 5,302,896 | 4/1994 | Dechene et al. | 324/300 X |
| 5,371,464 | 12/1994 | Rapoport | 324/306 |
| 5,397,993 | 3/1995 | Tews et al. | 324/310 X |

FOREIGN PATENT DOCUMENTS

811124   3/1981   U.S.S.R. .

Primary Examiner—Walter E. Snow
Assistant Examiner—Roger C. Phillips
Attorney, Agent, or Firm—Ronald A. Koatz

[57] ABSTRACT

An apparatus for corring aqueous surfactant composition and sampling moisture content wherein the apparatus includes a device for delivering composition to a main collection port; a device for coring the composition in the main collection port to form a sample; a device for delivering the sample into an NMR sensor area; a device for measuring moisture level of the sample in the NMR sensor area; and a device for extracting the sample from the NMR sensor area or returning the sample to a main collection port which includes a cross feed piston assembly.

8 Claims, 9 Drawing Sheets

APPARATUS FOR ACCURATELY CONTROLLING MOISTURE LEVELS OF AQUEOUS SURFACTANT COMPOSITIONS DURING ON LINE PROCESSING INCLUDING A CROSS-FEED PISTON ASSEMBLY

BACKGROUND OF THE INVENTION

The present invention relates to a novel apparatus for accurately controlling moisture levels of aqueous surfactant compositions (e.g., personal wash or personal product compositions, detergent compositions etc.), without having to stop the process to measure water content (i.e., on-line processing). Moisture control can also be maintained in the aqueous slurry phase used in preparation of powder detergents. In one embodiment of the invention, the apparatus is useful for preparing personal wash formulations (e.g., toilet bar formulations). The toilet bar formulations may be pure soap formulations, pure synthetic surfactant formulations or formulations containing mixtures of both.

The final moisture content of an aqueous surfactant composition can be very critical. For example, the moisture content of a toilet bar composition (which is eventually processed into a material suitable for plodding and stamping) significantly effects the processing characteristics as well as the user properties of the final toilet bar product.

Thus, for example, if the toilet bar mixture has a low final moisture content, the product may not lather well, may crack too readily or may be difficult to process. Conversely, if the moisture content of the mixture is too high, processing problems may also arise (e.g., stickiness and softness).

Final moisture value of a toilet bar soap mixture is generally roughly calculated by allowing a mixer to heat the mixture to defined temperature levels for set periods of time and further calculating amounts of water that has evaporated. In U.S. Pat. No. 4,663,070 to Dobrovolny et al. moisture levels were estimated based on viscosity of the soap blend in the mixer. Although these methods are on-line methods for calculating moisture, they are not completely accurate because of raw material variations that include inaccuracies in the amounts of material charged to the mixer as well as variations in raw material quality.

Accordingly, if a way could be found to measure final moisture content directly in the mixer, this would greatly enhance the accuracy with which water content could be measured and allow applicants to more greatly control the processing, the final use properties, and the physical properties of the toilet bar or personal washing composition.

The apparatus of the invention is not limited to use in personal washing compositions however, and can be used for the preparation of any aqueous surfactant composition in which it is required or it would be useful to know moisture content without stopping production. Thus, for example, it could be used to control moisture levels for personal product compositions (e.g., shampoos), detergent compositions (i.e., laundry compositions) and fabric care compositions among others.

Soviet Union Patent 811,124 discloses a method of controlling moisture in food samples. In the apparatus used therein, however, the samples must be weighed and then compared to a standard which must also be analyzed. This is not an on-line process. Thus the process is different. Moreover, the art (i.e. food) is non-analogous.

BRIEF SUMMARY OF THE INVENTION

Applicants have now discovered that moisture content of aqueous surfactant compositions can be controlled directly on line by utilizing an on line sampling device or apparatus which samples small portions of the mixture (the mixture may be viscous or non-viscous mixture having a viscosity from as low as 5 centipoise to as high as 1,000,000 centipoise) into a sensor unit (e.g., NMR sensor unit) and which sensor unit in turn calculates moisture values using nuclear magnetic resonance technology. The material is then returned by the sampling device to the process stream or vessel. Rather than put it back into the process stream, the sample may be discharged for external analysis of moisture levels (e.g., to further calibrate the device).

Utilizing the information gathered from the sampled medium, the sensor can calculate instantly when the proper/desired moisture content has been reached so that the mixture can be released for additional processing (e.g., plodding and stamping in the case of toilet bar compositions). More specifically, the sensor measures NMR parameters of the sample and compares the parameters to a preset calibration curve to obtain desired moisture levels.

The apparatus allows material to be extracted for measurement from processes that are operating at normal ambient pressures and temperatures as well as from sealed vessels, operating under vacuum or pressure at elevated or depressed temperatures. It allows periodic collection of samples of very viscous or solid like materials which are measured using a relatively small, inexpensive sensor and associated apparatus to determine the moisture level. In addition, the apparatus may provide samples of the process material for external measurements and it returns all other material to the process vessel after each NMR measurement.

DESCRIPTION OF FIGURES

FIG. 3 also shows the sensor assembly 13, the sensor magnet 14, the sensor coil 15 and the sample extraction port 16.

FIG. 5 is an end view showing the sampling device in the "clear position". The main piston 5 is fully extended and no product may enter the main collection cylinder 3. The facing ends of cross feed pistons 10a and 10b are located outside the inner bore of cylinder 3.

DETAILED SUMMARY OF THE INVENTION

The present invention relates to an apparatus for controlling levels of moisture in aqueous surfactant compositions.

More particularly, the present invention relates to an apparatus which can be used, while the ingredients forming the aqueous surfactant composition are mixed, to efficiently and accurately determine the moisture control of the mixture to a desired level ±0.5% of target moisture levels, preferably ±0.1%. This is in contrast to the previous methods of moisture control in which moisture is controlled by monitoring temperatures and levels of water evaporated (i.e., were not measured by an on-line apparatus) or by estimating moisture based on viscosity (i.e., were not accurate).

More specifically the invention provides a sampling instrument which extracts samples of compositions from a mixer or vessel being used to prepare aqueous surfactant compositions (e.g., toilet bar soaps or personal wash compositions) and utilizes an NMR sensor built into the sampling device to evaluate moisture content. Specifically, NMR parameters of the sample are measured and compared to a preset calibration curve to obtain desired moisture levels (i.e., NMR parameters are correlated to moisture level). The samples may then either be returned into the mixer or processing stream or they may be removed from the sampling device altogether for external analysis of moisture levels. Utilizing this sampling device allows one to automatically analyze moisture content of the composition on line and thereby determine exactly when a desired moisture level is reached. In the preparation of toilet bar soaps, for example, when desired moisture levels are accurately met, the mixture is ready to be dropped to a chill roll or other downstream area for further processing.

Generally, the apparatus comprises:

(a) a means for delivering composition to be sampled from a mixer or pipe or any place else the composition may be held into a main collection port (e.g., collection cylinder);

(b) a means for coring said composition in the collection port to form a sample;

(c) a means for delivering said cored sample into an NMR sensor area;

(d) a means for measuring moisture level of the sample in the NMR sensor area; and (e) a means for extracting sample from the NMR sensor area (e.g., for outside calibration) or for returning sample to main collection port.

As discussed in greater detail below, the composition is generally delivered from storage area using air pressure applied to pneumatic cylinders to provide the force needed to extract the composition. The delivery mechanism is not intended to be limited in this manner, however, and the composition may be delivered by forces produced by hydraulic means, mechanical means or any means such as are known to those skilled in the art. Extraction is generally accomplished through a piston attached to the storage area through which the composition is drawn. In general the piston surface is as near flush with the internal surface of the storage area/vessel wall as possible. To extract a quantity of material for measurement, the piston is moved to the opposite end of the collection cylinder to allow process material to flow into the collection pod or cylinder. The diameter of the collection cylinder is sufficient to permit even the most viscous or solid like materials to flow from the process vessel at an acceptable rate. For very viscous process materials a collection cylinder of large diameter may be required for rapid extraction of materials.

Subsequently, a means is used to core the composition in the collection port. Generally, this is done using a coring device air cylinder to push a coring device through the collection port to form a sample. The coring device may also be actuated however, hydraulically, mechanically or by any other means known to those skilled in the art.

It is especially useful to core a sample with regard to the viscous materials mentioned above. Recall that a collection cylinder of large diameter may be required to extract such materials. If one were to directly measure such large diameter samples without coring, this would require an NMR sensor (magnet and coil) which is bulky, heavy and expensive and would require associated electronic detection apparatus that is also very powerful and expensive.

To alleviate these requirements a "cross feed" mechanism is used to cut a small diameter cylindrical sample of the material that is in the collection port/cylinder and to push this sample into the NMR sensor for measurement. This sensor may be very compact, low in weight and inexpensive compared to that required to directly measure the material in the main collection cylinder. The cross feed mechanism consists of a cutter tube and a coaxial rod which are separately moved by an external mechanism such as pneumatic actuator. In may also be moved manually. Initially, during the material collection period, the cutter tube and piston are retracted outside the bore of the collection port/cylinder, but upon command the cutter tube is driven through the collected material across the diameter of the collector cylinder. Once the cutter tube bridges across the collector cylinder, the coaxial piston pushes the cylindrical sample through the cutter tube and then through an in-line sample feed tube into the NMR sensor.

In the NMR sensor area, moisture content is generally measured by pulsing the sample with an RF (resonant radio frequency) signal and then measuring the associated NMR parameters. These are known to those skilled in the art of NMR measuring.

Finally, there is a means for moving the sample from the NMR area either to an ejection port where it can be removed for calibration testing or back to the collection port. This is generally done using a cross feed assembly piston again although any suitable means may be used such as the hydraulic or mechanical means described above.

The cutter tube and coaxial piston are then returned to the initial position outside the bore of the collection cylinder. The piston in the main collection cylinder is then actuated to return all the collected process materials to the process vessel.

Figure 1:
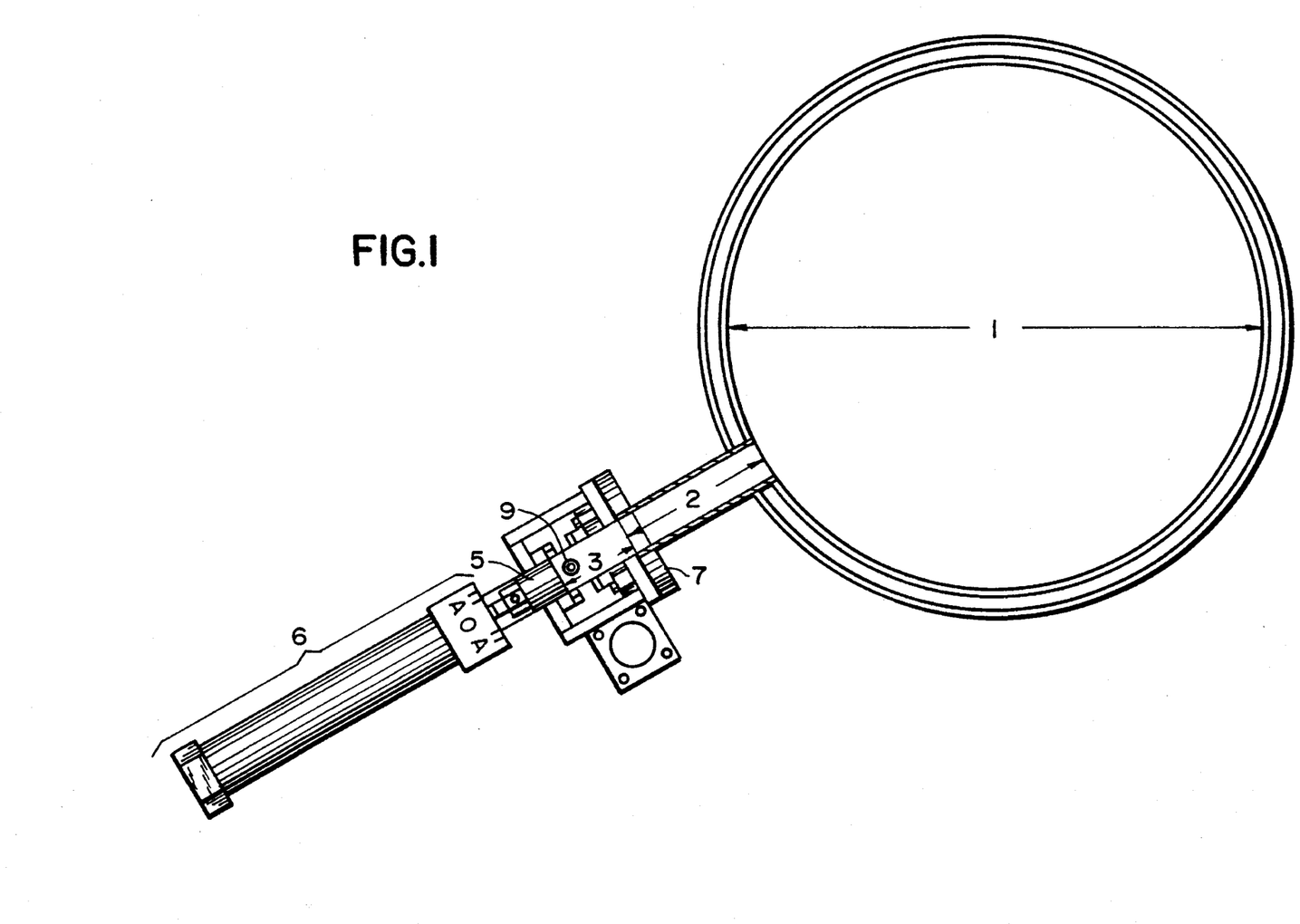
FIG. 1 is a side view of main piston 5 extracting sample from container 1 through pipe opening 2 into collection cylinder 3 from where a coring device 9 contained in a cross feed apparatus 4 (both seen in FIG. 2) will core a sample and a cross feed assembly piston 10a will feed the sample into a sensor 13 (also in FIG. 2).

Applicants refer now more particularly to FIG. 1, which represents a side view of the sampling device extracting sample from the mixer vessel or pipeline containing composition to be sampled. While the figures refer to extracting sample from this particle mixer or pipeline, it should be understood that the sampling device can be attached to the appropriate place for mixture control in different compositions. Thus, if the moisture level of the aqueous slurry used to make powder detergents needs to be controlled, the sample may be attached to, for example, the slurry tank or other suitable area.

Referring now to FIG. 1, a main piston 5 is found in a pipe opening 2 as close to the pipe as the connecting rod and piston in linear actuator 6 will allow (there is an opening in flange 7 which allows main piston 5 to go through the flange and be placed as close to pipe 1 as the linear range of actuator 6 will allow).

Main piston 5 is drawn backwards by pneumatic actuator 6 using air pressure applied to actuator 6 such that main piston 5 is brought back through pipe opening/extension 2. Piston 5 is drawn through the opening in flange 7 until it creates a main collection region in cylinder 3 where composition sample from pipe 1 will be drawn for measurement. Main piston 5 must be drawn far enough back so that it will sit behind the point where coring device 9 (seen more clearly in FIGS. 2 and 3) will be able to push through the diameter of the material in cylinder 3 to cut a sample which may be pushed into or through the NMR sensor.

Once the composition has been drawn into and through the opening 2 and the flange 7 into collection cylinder 3, a cross feed apparatus 4 (seen in more detail in FIGS. 2 and 3) is used to push or drive the composition from collection cylinder 3 into an NMR sensor 13 (see FIG. 2) where moisture content is measured and the sample is either returned to main collection cylinder 3 or pushed further through the sensor to an ejection pod 16 for external sampling. If returned to collection cylinder 3, the linear actuator 6 can then use air pressure to push main piston 5 back though the opening in flange 7 and as far into pipe opening 2 as the travel range of actuator 6 will allow.

Figure 2:
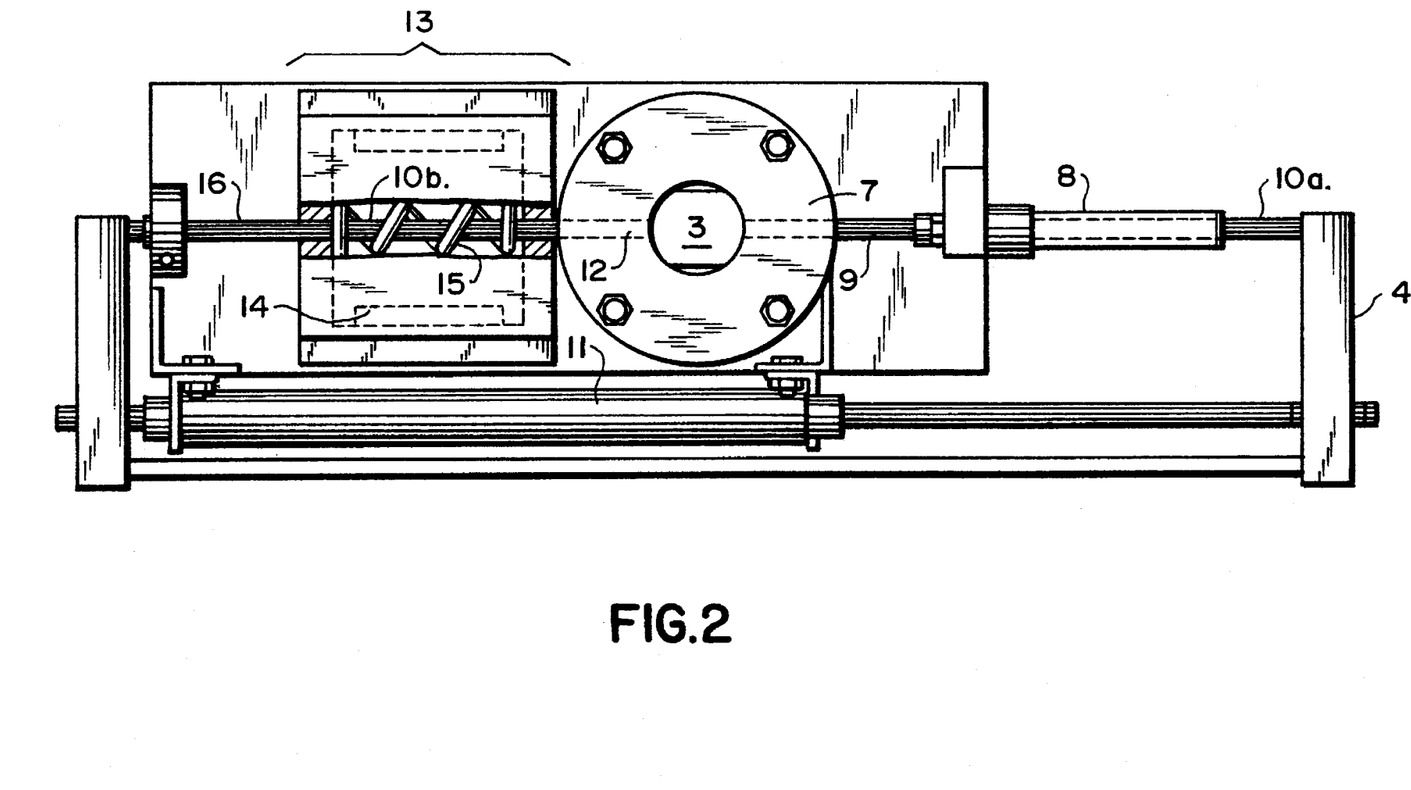
FIG. 2 is an end view of the coring device 9 and cross feed assembly piston 10a pushing the sample from collection cylinder 3 into the sensor assembly 13 for moisture evaluation.

Referring to FIG. 2, opening 3 is a view looking from pipe opening 2 into collection port 3 through the flange 7. 8 is the corring device air actuator which, when activated, pushes the coring device 9 through the main collection cylinder 3 and forms a sample. Cross feed assembly air actuator 11 is used to activate cross feed assembly piston 10a through coring device 9 thereby pushing the aforementioned sample into the NMR sensor 13. Sample is thereby pushed into the NMR sensor coil 15 located in NMR magnet 14.

After measuring moisture content, the composition sample may then be automatically returned to main collection cylinder 3 by cross feed assembly piston 10b or the sample may be further pushed into ejection port 16 by cross feed assembly piston 10a where it may be removed for external testing. This is required both to monitor accuracy of results as well as to allow the NMR sensor device to be accurately calibrated.

Figure 3:
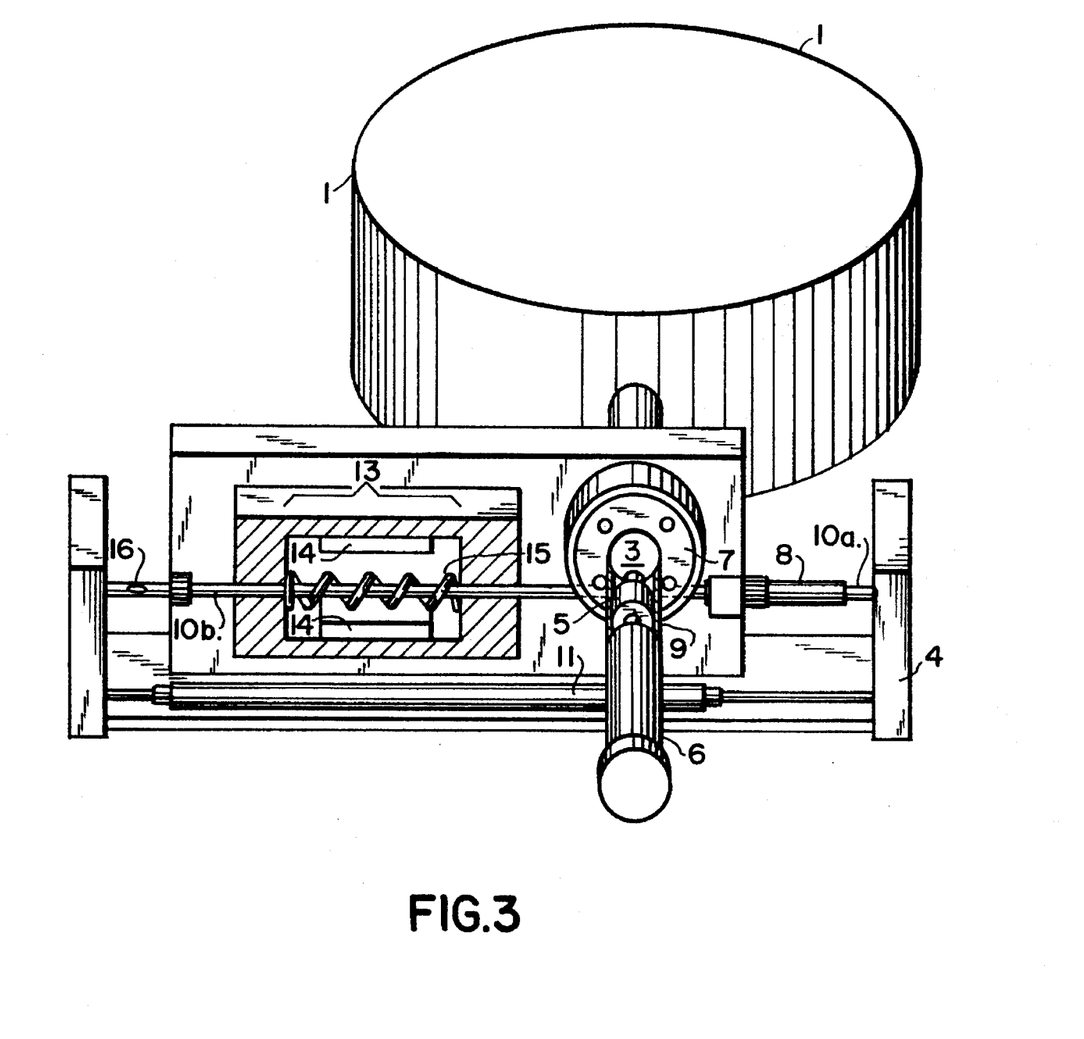
FIG. 3 is another end view similar to FIG. 2 but viewed from above and showing the positioning of the air cylinder 6 which moves main piston 5 in main collection cylinder 3.

FIG. 3 is another end view similar to FIG. 2 but viewed from above and showing the positioning of piston air actuator 6.

Referring to FIGS. 1, 2 and 3, the following is a description of how the apparatus is used:

(1) The main piston 5 in the fully extended position is retracted away from the mixer (process vessel,etc.) and process material then flows into the main collection cylinder 3.

(2) The coring device 9 is actuated and slides to the left and diametrically through the process material collected in the main collection cylinder 3 independent of the cross feed assembly pistons 10a and 10b to form a core sample of the material.

(3) The cross feed assembly piston 10a is then actuated to the left so that it passes through the coring device 9, thereby pushing the core sample through the cross feed sample tube 12 and into the region surrounded by the radio frequency (RF) coil 15 in the NMR sensor 13.

(4) NMR readings are taken and the sample can be either:

Extracted: The cross feed assembly piston 10a is then actuated further to the left, and the core sample is pushed through the ejection port 16; or Returned to the mixer (process vessel, etc.): The cross feed assembly piston 10 is then actuated to the right and the sample is pushed by piston 10b back into the main collection cylinder 3; and The coring device 9 is then retracted, and the main piston 5 is returned to its fully extended position, thus returning the sample to the mixer 1.

Figure 4A:
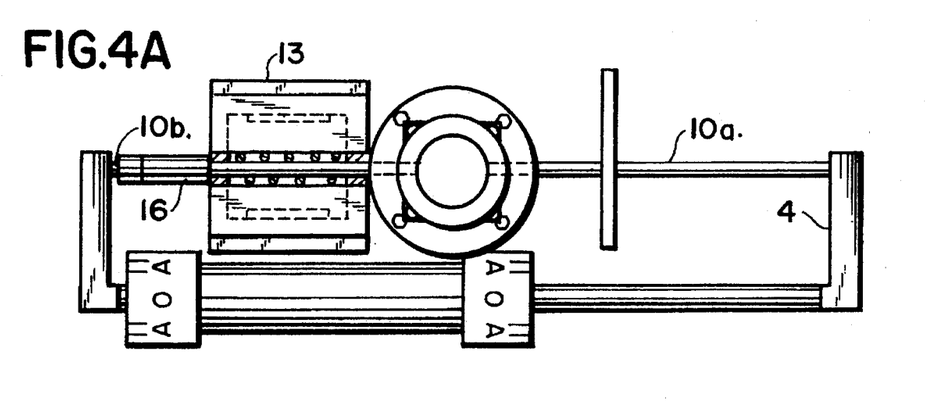
FIGS. 4A–4C are side views of a sample being pushed into the NMR sensor and of the sample being further extracted for external testing.
Figure 4B:
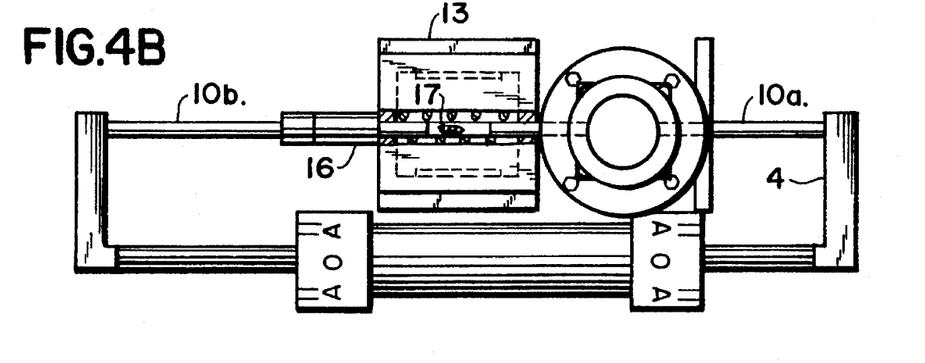
Figure 4C:
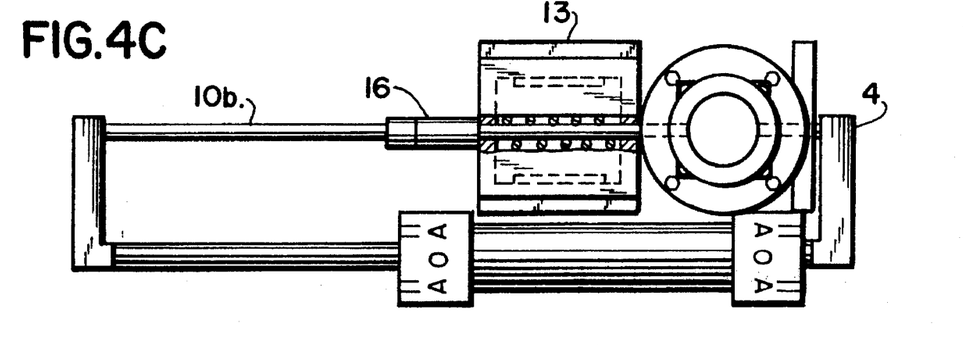
Figure 5:
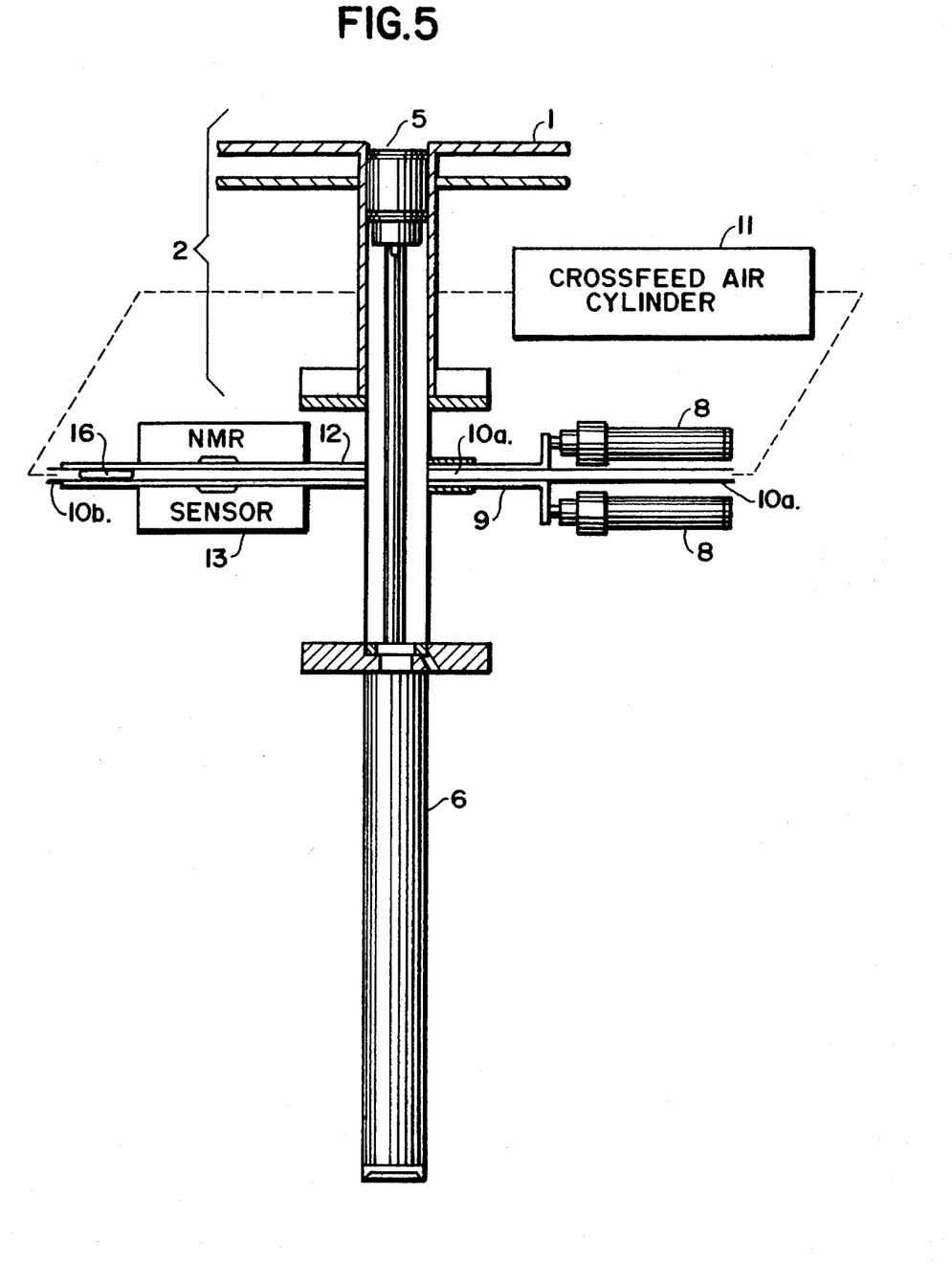
Figure 6:
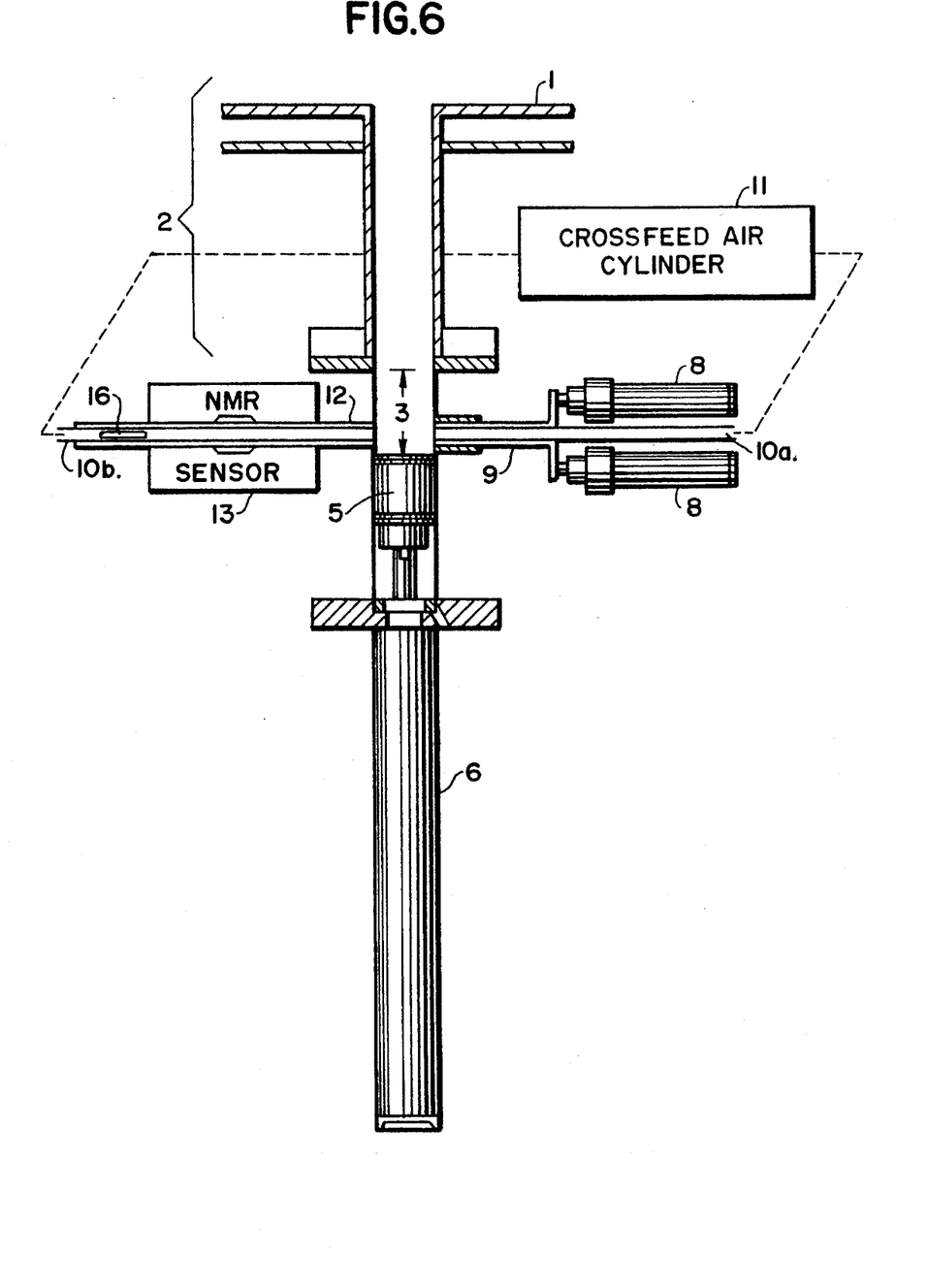
FIG. 6 shows the main piston 5 retracted, allowing the process material to flow into the main collection cylinder 3.
Figure 7:
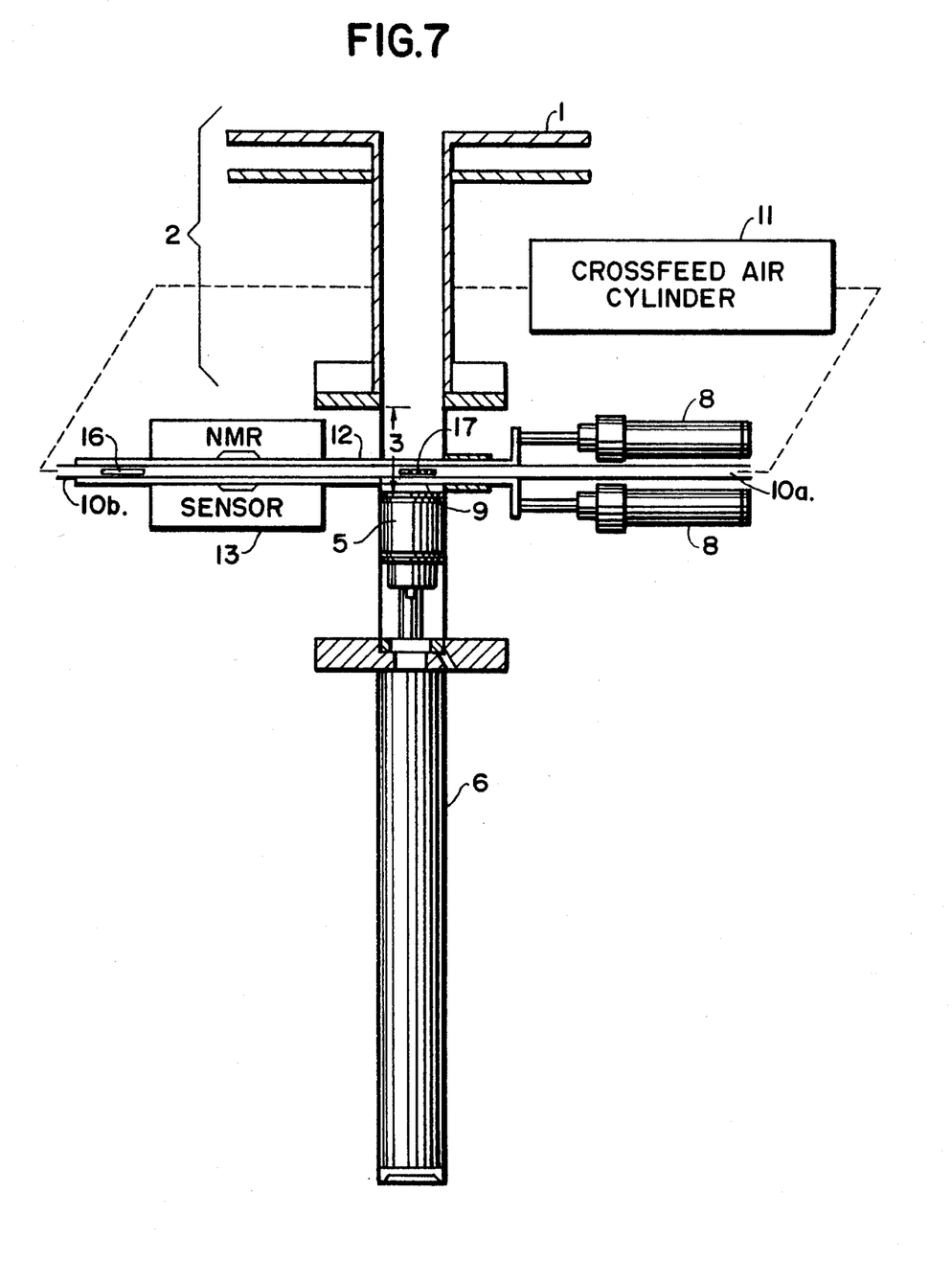
FIG. 7 shows the coring device 9 actuated to the left by cylinders 8 to form a core sample 17 that is located between the facing surfaces of cross feed pistons 10a and 10b.
Figure 8:
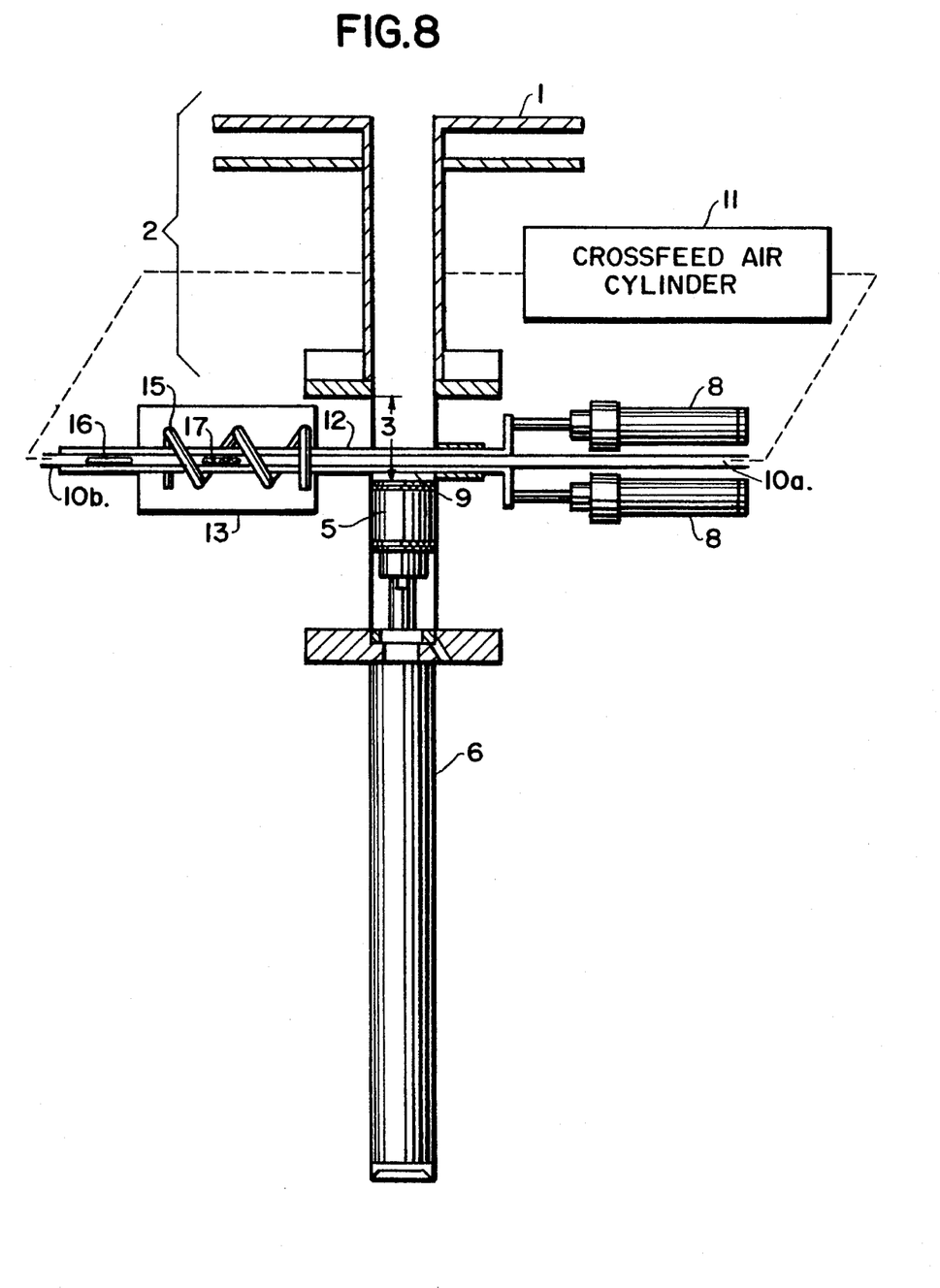
FIG. 8 shows the cross feed assembly piston 10a after it has been actuated by cylinder 11 to the left passing through the coring device 9 to push sample 17 into the NMR sensor coil 15.
Figure 9:
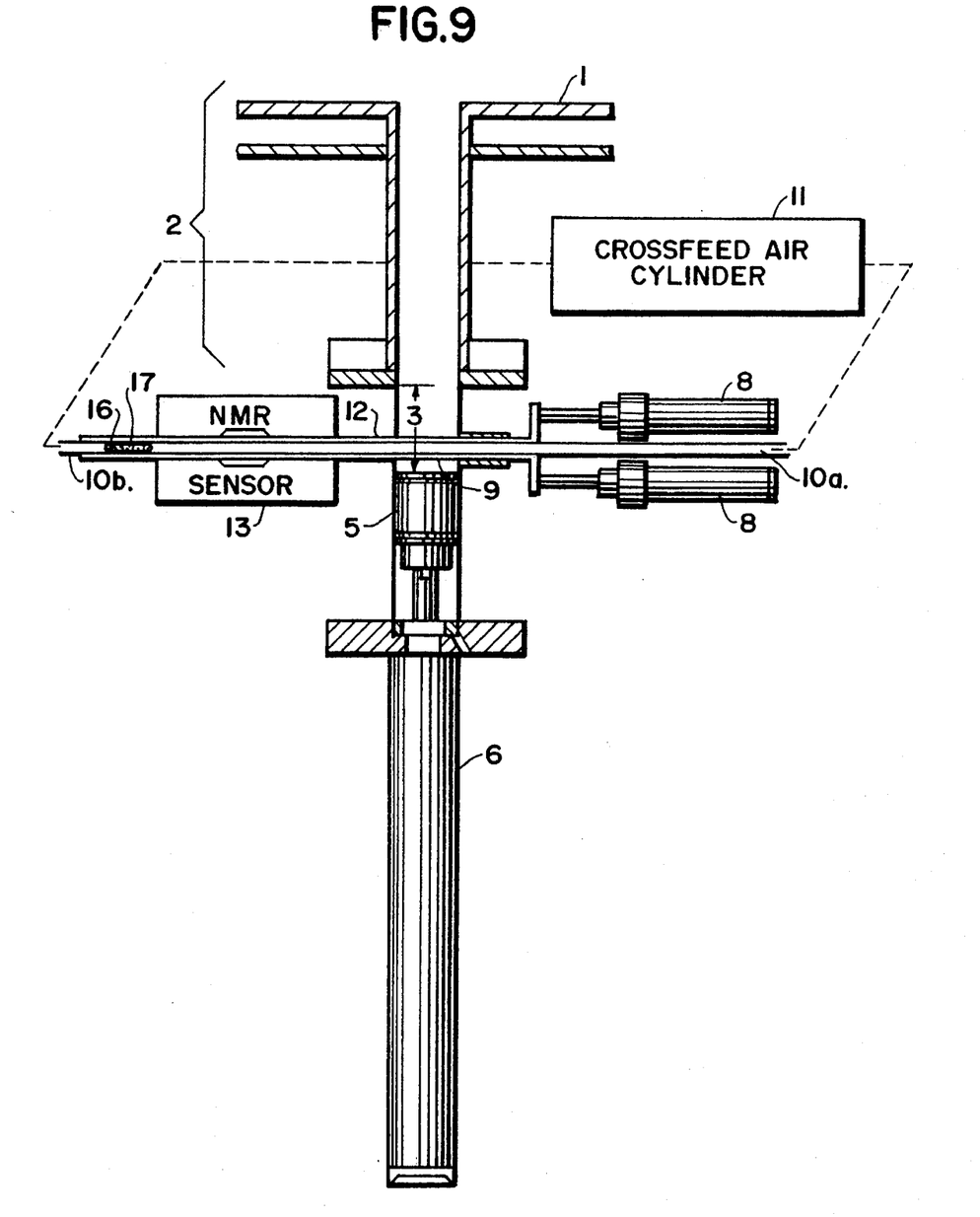
FIG. 9 shows the cross feed assembly piston 10a after it has been actuated all the way to the left and has pushed the sample 17 to the ejection port 16 where it can be removed from the sampling device. The sample 17 can be returned to the storage vessel if an external sample is not necessary. In order to return the sample to the storage vessel, the cross feed assembly piston 10b is actuated all the way to the right, the coring device 9 is retracted, and then the main piston 5 is returned to its fully extended position.

FIG. 4 is again an end view looking down from pipe opening 2 into main collection cylinder 3. In FIG. 4a, the main collection port is assumed to be filled. FIG. 4b shows how cross feed assembly piston 10, actuated by piston 11, pushes a sample through the corring device into the NMR sensor region. The sample can be extracted from the sensor to provide external analysis (FIG. 4c).

Using the apparatus of the invention, the moisture level of the sample is checked or compared to a preset desired moisture level (i.e., a preset calibration curve which correlates NMR parameters to desired moisture levels) and the sample is released for further processing when the desired level is obtained.

It should be noted that this invention is superior to any moisture controlling method used in the art in that no pre-weighing is required to determine moisture levels (e.g, as in the Karl-Fisher method or in the Soviet patent discussed above). Further, it is a very exact method for measuring water content on line as compared to other on-line methods which are much more inaccurate.

As noted above, the compositions used in the apparatus of the invention can be any aqueous surfactant mixture whether the aqueous surfactant mixture is used to make a final liquid product (i.e., aqueous detergent compositions) or whether it be used to make powder detergents (i.e., aqueous slurries used to make powder) or bar soaps. The term surfactant is defined to include soap.

In its broadest form, the aqueous surfactant composition may contain about 5% to about 95% by weight surfactant and about 5% to 95% by weight water. The range of surfactant and water will, of course, vary depending on the product. For example, bars normally will contain no more than 30% initial water (initial is meant water in the starting mixture) wherein liquid soap may contain up to 80% by weight water. Other compositions contain amounts of water such as would be well known to those skilled in the various compositions.

The key to the invention, however, is not in the process definition of the amounts of water or surfactant, but in the ability to accurately control desired moisture levels, whatever they may be, on-line. It is believed that the accurate, on-line control of moisture levels in aqueous surfactant compositions (e.g., personal wash, personal product, liquid detergent, aqueous slurries used to make powder, and fabric care compositions) is unknown and applicants should be entitled to broad coverage of composition ranges in this regard.

With regard to personal wash or toilet bar compositions, the compositions used in the apparatus of this invention may contain a certain amount of "soap" (as noted above, surfactant compositions are intended to encompass soap) which herein is meant to be alkali metal salts of aliphatic alkane- or alkene monocarboxylic acids, more generally known as $C_{12}$–$C_{22}$ alkyl fatty acids. Sodium and potassium salts are preferable. Alkanolammonium salts such as those formed from triethanolamine have certain deficiencies which are not considered useful for this invention and are therefore outside its scope. A preferred soap is a mixture of about 15% to about 45% coconut oil and about 55% to about 85% tallow.

The soaps may contain unsaturation in accordance with commercially acceptable standards. Excessive unsaturation is normally avoided.

The amount of soap used in the soap compositions of the present invention is not limited and the invention may be used with compositions having up to 100% soap (excluding minors such as preservatives, dyes, etc.) or having no soap at all.

Soap formulations encompassed by this invention may either be in liquid, gel or toilet bar form.

Generally, the personal product or toilet bar compositions of the invention will also contain non-soap surface active agent, or syndet. Again, the bar may contain 100% non-soap surface active or may contain 0% non-soap surface again or any range in between.

The non-soap active is generally chosen from the group consisting of anionics, nonionics, cationics, amphoterics and mixtures thereof. Generally, combination of anionics and amphoterics are preferred, particularly if mildness is desirable.

Among suitable anionic co-actives are the alkyl ether sulfates, alkyl ether sulfonates, sarcosinates, sulfosuccinates, taurates and combinations thereof. Among suitable amphoteric co-actives may be included alkyl betaines, amidopropyl betaines, amidopropyl sultaines and combinations thereof.

Alkyl ether sulfates of this aspect of the present invention will be of the general formula $R-O(CH_2CH_2)_nOSO_3-M+$ wherein R ranges from $C_8-C_{20}$ alkyl, preferably $C_{12}-C_{15}$ alkyl, n is an integer from 9 to 40, preferably from 10 to 20, optimally about 12, and M+ is a sodium, potassium, ammonium or triethanolammonium cation.

Typical commercial co-actives of this variety are listed in the Table below:

| Trademark | Chemical Name | Physical Form | Manufacturer |
|---|---|---|---|
| Alkasurf ES-60 | Sodium Laureth Sulfate | Paste | Alkaril |
| Cycloryl TD | TEA Laureth Sulfate | Paste | Cyclo |
| Standapol 125-E | Sodium Lauareth-12 Sulfate | Liquid | Henkel |
| Cedepal TD407MF | Sodium Trideceth Sulfate | Paste | Miranol |

Alkyl ether sulfonates may also be employed in the embodiment of the present invention. Illustrative of this category is a commercial product known as Avenel S-150 commonly known as a sodium $C_{12}-C_{15}$ Pareth-15 sulfonate.

Another co-active type suitable for use in the this embodiment of the present invention is that of the sulfosuccinates. This category is best represented by the monoalkyl sulfosuccinates having the formula: $RO_2CCH_2CH(SO_3-Na^+)COO-M^+$; and amido-MEA sulfosuccinates of the formula: $RCONHCH_2CH_2O_2CCH_2CH(SO_3-M^+)CCO-M^+$; wherein R ranges from $C_8-C_{20}$ alkyl, preferably $C_{12}-C_{15}$ alkyl and M+ is a sodium, potassium, ammonium or a triethanolammonium cation. Typical commercial products representative of these co-actives are those listed in the Table below:

| Trademark | Chemical Name | Physical Form | Manufacturer |
|---|---|---|---|
| Emcol 4400-1 | Disodium Lauryl Sulfosuccinate | Solid | Witco |
| Schercopol CMSNa | Disodium Cocoamido MEA Sulfosuccinate | Liquid | Scher |
| Emcol 4100M | Disodium Myristamido MEA Sulfosuccinate | Paste | Witco |
| Schercopol | Disodium Oleamido MEA | Liquid | Scher |
| Varsulf S13333 | Disodium Recinoleamido MEA Sulfosuccinate | Solid | Scherex |

Sarcosinates may also be useful in the present invention as a co-active. This category is indicated by the general formula $RCON(CH_3)CH_2CO_2-M^+$, wherein R ranges from $C_8-C_{20}$ alkyl, preferably $C_{12}-C_{15}$ alkyl and M+ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Hamposyl L-95 | Sodium Lauroyl Sarcosinate | Solid | W. R. Grace |
| Hamposyl TOC-30 | TEA Cocoyl/ Sarcosinate | Liquid | W. R. Grace |

Taurates may also be employed in the present invention as co-actives. These materials are generally identified by the formula $RCONR'CH_2CH_2SO_3-M^+$, wherein R ranges from $C_8-C_{20}$ alkyl, preferably $C_{12}-C_{15}$ alkyl, R' ranges from $C_1-C_4$ alkyl, and M+ is a sodium, potassium, ammonium or triethanolammonium cation. Typical commercial products representative of these co-actives are those listed in the Table below:

| Trademark | Chemical Name | Physical Form | Manufacturer |
|---|---|---|---|
| Igepon TC 42 | Sodium Methyl Cocoyl Taurate | Paste | GAF |
| Igepon T-77 | Sodium Methyl Oleoyl Taurate | Paste | GAF |

Within the category of amphoterics there are three general categories suitable for the present invention. These include alkylbetaines of the formula $RN^+(CH_3)_2CH_2CO_2-M^+$, amidopropyl betaines of the formula $RCONHCH_2CH_2CH_2N^+(CH_3)_2CH_2CO_2-M^+$, and amidopropyl sultaines of the formula $RCONHCH_2CH_2N^+(CH_3)_2CH_2SO_3-M^+$, wherein R ranges from $C_8-C_{20}$ alkyl, preferably $C_{12}-C_{15}$ alkyl, and $M^+$ is a sodium, potassium ammonium or triethanolammonium cation. Typical commercial products representative of these co-actives are found in the Table below:

| Trademark | Chemical Name | Physical Form | Manufacturer |
|---|---|---|---|
| Lonzaine C | Cocamidopropyl Betaine | Liquid | Lonza |
| Lonzaine CS | Cocamidopropyl Hydroxysultaine | Liquid | Lonza |
| Lonzaine 12C | Coco-Betaine | Liquid | Lonza |
| Schercotaine MAB | Myristamidopropyl Betaine | Liquid | Lonza |
| Vellvetex OLB-50 | Oleyl Betaine | Paste | Henkel |

Within the broad category of actives, the most effective are the alkyl sulfates, alkyl ether sulfates, alkyl ether sulfonates and sulfosuccinates.

As noted above, if mild bars are desired, it is preferable to use mild surfactants, especially mild anionic and amphoteric surfactants.

Preferred mild anionic and amphoteric surfactants used in this invention include suitable alkyl glyceryl ether sulfonate (AGS), anionic acyl sarcosinates, methyl acyl taurates, N-acyl glutamates, acyl isethionates, alkyl sulfosucinate, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 2 ethoxy groups, especially ammonium and sodium lauryl ether sulfates. Alkyl chains for these surfactants are $C_8-C_{22}$, preferably $C_{10}-C_{18}$ Alkyl glucosides and methylglucose ethers are preferred mild nonionic which may be mixed with at least one of said mild anionic or amphoteric surfactants in the compositions of this invention.

One preferred primary mild surfactant is sodium coco glyceryl ether sulfonate. If lather creaminess is desired, a sodium 90/10 coconut/tallow alkyl AGS distribution is preferred for such creaminess. Salts other than the sodium salt such as TEA-, ammonium and K-AGS and chain length distributions other than 90/10 coconut/tallow are usable at moderate levels. Also, some soap may be added to improve lather volume and speed of lathering. Certain secondary co-surfactants used in combination with AGS can also provide a creamier and more stable lather. These secondary surfactants should also be intrinsically mild. One secondary surfactant that has been found to be especially desirable is sodium lauroyl sarcosinate (trade name Hamposyl L, made by Hampshire Chemical).

The amphoteric betaines and sultaines can be used as the sole surfactant in mild bars but are more preferred as a co-surfactant. Nonionics should generally not be used as the sole surfactant because of their low foaming ability; however, they can be incorporated as a co-surfactant.

Other mild surfactants are discussed in U.S. Pat. No. 4,812,253 to Small et al., hereby incorporated by reference into the subject application.

One particularly desirable synthetic surfactant is the $C_{8-20}$ acyl isethionates. These esters may be prepared by the reaction between alkali metal isethionate and mixed aliphatic fatty acids having from 8 to 22 carbon atoms and an Iodine Value of less than 20. At least 75% of the mixed fatty acids should preferably have from 12 to 18 carbon atoms and up to 25% should have from 8 to 10 carbon atoms.

Among the many nonionics and cationics which may be used are those discussed extensively in U.S. Pat. No. 3,761,418 to Parran, Jr. hereby incorporated by reference into the subject application.

Free fatty acids of 8–22 carbons may also be desirably incorporated within the compositions of the present invention. Some of these fatty acids are present to operate as superfatty agents and others as skin feel and creaminess enhancers. Superfattying agents enhance lathering properties and may be selected from fatty acids of carbon atoms numbering 8–18, preferably 10–16, in an amount up to 25% by weight of the composition. Skin feel and creaminess enhancers, the most important of which is stearic acid, are also desirably present in these compositions. Levels of stearic acid can range from 0% up to 40%, preferably between 5% and 25%.

Other performance chemicals and adjuvants may be needed with these compositions. The amount of these chemicals and adjuvants may range from about 0% to about 40% by weight of the total composition. Illustrative of these materials are perfumes, pigments or dyes, preservatives, electrolyte salts, water and mixtures thereof.

Other embodiments of the invention (i.e., other than personal wash compositions and bar soap compositions) also comprise surfactants which may be soap, anionic (other than soap), nonionic, cationic, zwitterionic or amphoteric detergent materials or mixtures of any of these.

These compositions can all contain ingredients associated with those particular compositions, for example, liquid detergent compositions will typically contain surfactant mixtures, detergency builders and optional ingredients such as enzymes, polyacids, suds regulants, opacifiers, antioxidants, bactericides, dyes, perfumes, brighteners and the like.

The following examples will more fully illustrate the embodiments of this invention. The examples are for illustrative purposes only and are not intended to limit the claims in any way. All parts, percentages and proportions referred to herein and in the appended claims are by weight of the total composition unless otherwise stated.

EXAMPLE 1

A toilet bar having the composition below was prepared using the apparatus and the process of this invention.

TABLE 1

| Toilet Bar Formulation Containing Soap/Acyl Isethionate | |
|---|---|
| Components | Weight % |
| Sodium soap | About 50% |
| Sodium cocoyl isethionate | About 20% |
| Water (final content) | About 10% |
| Fatty acids | About 5–10% |
| Sodium isethionate | About 5% |
| Miscellaneous (perfume, colorants, preservatives) | About 3% |

It should be understood that this was one of thousands of formulations which may be used including pure soap bar formulations. That is, the invention is not really limited by the formulation. Rather, it is an apparatus and method of controlling moisture in aqueous surfactant compositions.

In this example, toilet bars having the formulation noted above were made using a Drais Mixer. The mixer was preheated with steam while the ingredients were charged. The batch was then mixed while being heated under vacuum to expedite the drying process. Samples of the batch were extracted from the mixer, using the sampling device described earlier, placed in the NMR sensor region and analyzed for moisture content. The samples were then expelled from the sampling device into containers and analyzed for moisture content using standard laboratory techniques such as Karl Fisher titration. The Karl Fisher moisture data was used to initially calibrate the sensor.

The NMR sensor measures the total amount of hydrogen present and then correlates this information with a present calibration curve to accurately predict the amount of moisture present in the batch. Many NMR laboratory methods for measuring moisture require that the sample be weighed. In this invention it was found that, using hydrogen NMR, a ratio of the Hahn Echo NMR signal voltage amplitude to the FID (free induction decay signal) NMR signal voltage amplitude worked very well to accurately predict moisture content. These readings do not require that a sample be weighed in order to measure moisture. This is a significant advantage for an on line sensor.

Samples were taken approximately every 1–2 minutes as the batch was dried in the mixer. When the Hahn Echo/FID ratio signal reached a preset number, as determined by a calibration curve, the batch was dropped. There is an extremely broad correlation between the Hahn Echo/FID signal and the Karl Fisher titration. The sensor predicted moisture well within ±0.5% over a wide range of product moisture as the mixture was dried from about 20% to 5%. In some cases, correction of the Hahn Echo/FID ratio for the effects of changes in the hydrogen NMR spin spin relaxation time $T_2$ may need to be utilized for improved accuracy in the moisture determination. One such correction is based on the relation $$\text{weight \% H}_2\text{O} = \frac{K_1 V_H}{V_F - K_2 V_H}$$

where $V_H$ is the peak voltage amplitude of the Hahn Echo, $V_F$ is the peak amplitude of the FID signal, $K_1$ is a calibration constant and $K_2$ is a correction factor that is a function of $T_2$ of the product. This is also within the scope of the invention.

When the desired moisture level was obtained, the reactant mixture is released from the Drais Mixer onto a doctor roll hopper of a chill roll where the blend is cooled into chips and the chips are passed on for further processing.

EXAMPLE 2

A pure soap bar composition having the composition set forth below may be prepared in the apparatus of this invention.

|  | % by wt. |
| --- | --- |
| Soap | about 85% |
| other ingredients (perfume, water) | about 15% |

EXAMPLE 3

A toilet bar having the following composition may be prepared in the apparatus of the invention.

| Ingredients | % |
| --- | --- |
| Acyl esters of isethionic acid salt | 30–70% |
| Amido sulfosuccinate | Ratio of acyl ester to sulfosuccinate is 6:1 to 2:1 |
| Free fatty acid | 2–40% |
| Fatty alcohol | 0–10% |
| Sodium isethionate | 2–20% |
| Soap | 0–10% |
| Water | 2–20% |

EXAMPLE 4

A toilet bar soap having the following composition may be prepared in the apparatus of the invention.

| Ingredients | % |
| --- | --- |
| Coco fatty acid isethionate | about 50% |
| Fatty acids | about 2.5% |
| Sodium isethionate | about 5% |
| Soap | about 11% |
| Other ingredients (perfume, water, etc.) | about 9% |

EXAMPLE 5

A toilet bar soap having the following composition may be prepared in the apparatus of the invention.

| Ingredients | % |
| --- | --- |
| Coco fatty acid isethionate | about 50% |
| Fatty acids | about 25% |
| Sodium isethionate | about 6% |
| Cocoamidosulfosuccinate | about 6% |
| Cocoamidopropyl betaine | about 2% |
| Other ingredients (perfume, water etc.) | about 11% |

EXAMPLE 6

The liquid soap composition having the following composition may be prepared in the apparatus of the invention.

| Ingredients | % |
| --- | --- |
| Sodium cocoyl isethionate | 3 to 20% |
| A mixture of about 55% palmitic acid and about 45% Stearic acid | 2 to 15% |
| Propylene glycol | 5 to 15% |
| Sodium isethionate | 1 to 8% |
| TEA lauryl sulfate | 1 to 5% |
| Sodium soap | 1 to 5% |
| Sodium alkylbenzene sulfonate | 1 to 5% |
| p hydroxy methyl benzoate | 0.1 to 1% |
| p hydroxy propyl benzoate | 0.1 to 1% |
| N-(3 chorally) Hexaminium chloride | 0.1 to 1% |
| EDTA | 0.01 to 0.5% |
| EHDP | 0.01 to 0.5% |
| BHT | 0.01 to 1.0% |

We claim:

1. An apparatus for controlling moisture content of aqueous surfactant compositions which apparatus comprises:
   (a) means for delivering composition to a main collection port;
   (b) means for forming a sample of said composition;
   (c) means for delivering said sample into an NMR sensor area using a cross feed assembly piston, said NMR sensor area being in an area separate from said main collection port; and;
   (d) means for measuring the amount of water in said sample in said separate NMR sensor area.

2. An apparatus according to claim 1, wherein composition is delivered to the main collection port by utilizing air pressure to extract composition from a main mixer to said main collection port.

3. An apparatus according to claim 2, wherein composition is extracted through use of a piston.

4. An apparatus according to claim 1, wherein said means of forming a sample comprises using a means for coring said composition in said main collection port to form sample.

5. An apparatus according to claim 4, wherein said means for coring comprises a coring device or cylinder which, when activated, push a coring device through said main collection port to form a sample.

6. An apparatus according to claim 1, wherein said cross feed assembly piston of step (c) is activated by a cross feed assembly air cylinder.

7. An apparatus according to claim 1, wherein, after the amount of water in said sample has been measured in said separate NMR sensor, said cross feed assembly piston is used to extract sample to an ejection port for external sampling.

8. An apparatus according to claim 1, wherein, after the amount of water in said sample has been measured in said separate NMR sensor, said cross feed assembly piston is used to return sample to said main collection port.

* * * * *